United States Patent
Gong et al.

(10) Patent No.: US 11,779,308 B2
(45) Date of Patent: Oct. 10, 2023

(54) ULTRASOUND DIAGNOSIS APPARATUS AND METHOD OF MANAGING ULTRASOUND IMAGE OBTAINED THEREBY

(71) Applicant: SAMSUNG MEDISON CO., LTD., Hongcheon-gun (KR)

(72) Inventors: Soyeon Gong, Seongnam-si (KR); Jaesung Lee, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 390 days.

(21) Appl. No.: 17/091,301

(22) Filed: Nov. 6, 2020

(65) Prior Publication Data
US 2021/0219946 A1 Jul. 22, 2021

(30) Foreign Application Priority Data

Jan. 22, 2020 (KR) ........................ 10-2020-0008748

(51) Int. Cl.
*A61B 8/00* (2006.01)
*A61B 8/08* (2006.01)

(52) U.S. Cl.
CPC ............ *A61B 8/465* (2013.01); *A61B 8/4254* (2013.01); *A61B 8/463* (2013.01); *A61B 8/0825* (2013.01); *A61B 8/467* (2013.01); *A61B 8/5292* (2013.01)

(58) Field of Classification Search
CPC ....... A61B 8/465; A61B 8/4254; A61B 8/463; A61B 8/0825; A61B 8/467; A61B 8/5292;
(Continued)

(56) References Cited

U.S. PATENT DOCUMENTS

| 5,660,179 A | 8/1997 | Matsumoto et al. |
| 10,206,660 B2 | 2/2019 | Tashiro |

(Continued)

FOREIGN PATENT DOCUMENTS

| JP | 2000-254125 A | 9/2000 |
| JP | 2008-061935 A | 3/2008 |

(Continued)

OTHER PUBLICATIONS

Philips Healthcare "Interview with Dr Kinkel, Switzerland, about her experience with AI Breast" Youtube, Jun. 27, 2018 retrieved on Nov. 5, 2020, from https://www.youtube.com/watch?v=vHMU_DA7h6E#action=share (1 page total).

(Continued)

*Primary Examiner* — Yi-Shan Yang
*Assistant Examiner* — Nicholas A Robinson
(74) *Attorney, Agent, or Firm* — Sughrue Mion, PLLC

(57) ABSTRACT

An ultrasound diagnosis apparatus includes: a display displaying a body marker including a first type of first probe marker related to a first ultrasound image of an object; an image processor configured to obtain a second ultrasound image of the object; and a controller configured to identify a position of a probe used to obtain the second ultrasound image in the body marker and mark a second type of second probe marker on the body marker according to a result of comparing a position of the first type of first probe marker with the identified position, wherein the second type is different from the first type.

16 Claims, 14 Drawing Sheets

(58) Field of Classification Search
CPC ..... A61B 8/468; A61B 8/4245; A61B 8/4405; A61B 8/5223; A61B 8/461; A61B 8/54
See application file for complete search history.

(56) References Cited

U.S. PATENT DOCUMENTS

| | | |
|---|---|---|
| 2002/0167549 A1 | 11/2002 | Cupples et al. |
| 2014/0088427 A1 | 3/2014 | Tashiro |
| 2014/0221836 A1 | 8/2014 | Takeda et al. |
| 2016/0206283 A1 | 7/2016 | Ota |
| 2018/0360427 A1 | 12/2018 | Nakano et al. |

FOREIGN PATENT DOCUMENTS

| | | | |
|---|---|---|---|
| JP | 2008-104551 A | 5/2008 | |
| JP | 4490715 B2 | 6/2010 | |
| JP | 2014-064637 A | 4/2014 | |
| JP | 5958290 B2 | 7/2016 | |
| JP | 6538130 B2 | 7/2019 | |
| KR | 20180096342 A * | 8/2018 | ............. A61B 8/461 |

OTHER PUBLICATIONS

Communication dated Mar. 11, 2021, from the European Patent Office in European Application No. 20204285.9.

* cited by examiner

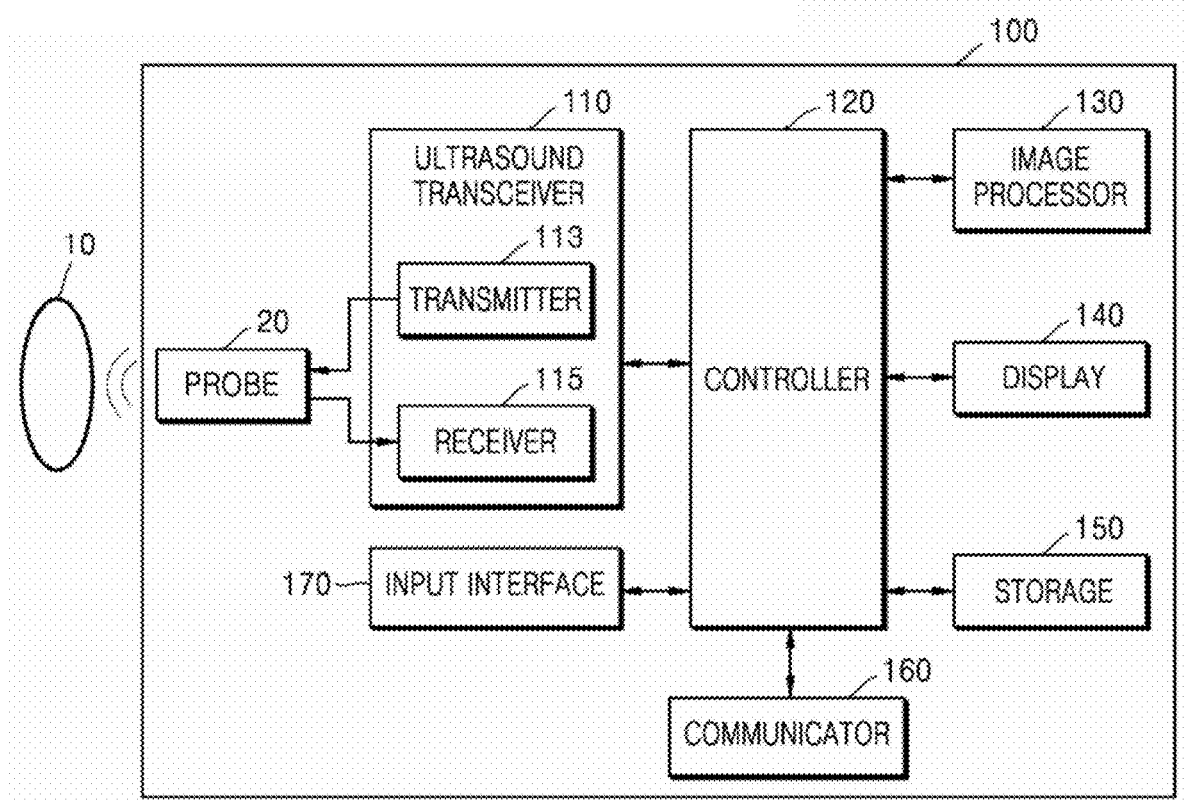

ULTRASOUND DIAGNOSIS APPARATUS AND METHOD OF MANAGING ULTRASOUND IMAGE OBTAINED THEREBY

CROSS-REFERENCE TO RELATED APPLICATION(S)

This application is based on and claims priority under 35 U.S.C. § 119 to Korean Patent Application No. 10-2020-0008748, filed on Jan. 22, 2020, in the Korean Intellectual Property Office, the disclosure of which is incorporated by reference herein in its entirety.

BACKGROUND

1. Field

The disclosure relates to a field of ultrasound imaging, and more particularly, to a method of managing an ultrasound image obtained by an ultrasound diagnosis apparatus.

2. Description of Related Art

Ultrasound diagnostic apparatuses transmit ultrasound signals generated by transducers of a probe to an object and detect information about signals reflected from the object, thereby obtaining at least one image of an internal part, for example, soft tissue or blood flow, of the object.

In general, a body marker tagged on an ultrasound image is used to indicate which part of an object is captured in an ultrasound image. The body marker includes a probe marker for indicating a part of the object at which a probe used for capturing the ultrasound image is located. By examining the ultrasound image and the probe marker included in the body marker, a user may easily recognize which part of the object is captured in the ultrasound image and in which direction the ultrasound image is captured.

SUMMARY

Provided are ultrasound diagnosis apparatuses and methods of managing an ultrasound image obtained by an ultrasound diagnosis apparatus, which are capable of efficiently managing the ultrasound image through a body marker and a probe marker.

Also provided are ultrasound diagnosis apparatuses and methods of managing an ultrasound image obtained by an ultrasound diagnosis apparatus, which allow a user to easily recognize a part having a high probability of being a lesion with only a body marker.

Also provided are ultrasound diagnosis apparatuses and methods of managing an ultrasound image obtained by an ultrasound diagnosis apparatus, which allow the user to easily retrieve ultrasound images captured from a part having a high probability of being a lesion.

Additional aspects will be set forth in part in the description which follows and, in part, will be apparent from the description, or may be learned by practice of the presented embodiments of the disclosure.

In accordance with an aspect of the disclosure, an ultrasound diagnosis apparatus includes: a display displaying a body marker including a first type of first probe marker related to a first ultrasound image of an object; an image processor configured to obtain a second ultrasound image of the object; and a controller configured to identify a position of a probe used to obtain the second ultrasound image in the body marker, and mark a second type of second probe marker on the body marker according to a result of comparing a position of the first type of first probe marker with the identified position, wherein the second type is different from the first type.

The controller may be further configured to mark the second type of second probe marker on the body marker when a distance between the position of the first type of first probe marker and the identified position is less than or equal to a threshold distance.

The threshold distance may be set based on manipulation by a user.

The controller may be further configured to delete the first type of first probe marker from the body marker.

The first type of first probe marker may indicate that the number of its related ultrasound images is 1, and the second type of second probe marker may indicate that the number of its related ultrasound images is two or more.

The second type of second probe marker may indicate a result value obtained by adding a number of first ultrasound image to a number of second ultrasound image.

The first type of first probe marker may include one head portion and one body portion, and the second type of second probe marker may include one head portion and the same number of body portions as the result value.

The second type of second probe marker may include a number corresponding to the result value.

The ultrasound diagnosis apparatus may further include a storage storing the body marker with the second type of second probe marker marked thereon and the first and second ultrasound images, and the controller may be further configured to display the stored body marker on the display according to a user's request to retrieve an image of the object, and when the second type of second probe marker is selected by the user from the body marker, obtain the first and second ultrasound images from the storage as ultrasound images related to the second type of second probe marker.

The image processor may be further configured to obtain a third ultrasound image of the object, the controller may be further configured to identify a position of the probe used to obtain the third ultrasound image in the body marker and change the second type of second probe marker to a second type of third probe marker according to a result of comparing a position of the second type of second probe marker with the identified position of the probe used to obtain the third ultrasound image, and the second type of third probe marker may indicate a value obtained by adding 1 to the result value.

In accordance with another aspect of the disclosure, a method of managing an ultrasound image includes: displaying a body marker including a first type of first probe marker related to a first ultrasound image of an object, and identifying a position of a probe used to obtain a second ultrasound image in the body marker and marking a second type of second probe marker on the body marker according to a result of comparing a position of the first type of first probe marker with the identified position, wherein the second type is different from the first type.

The marking of the second type of second probe marker on the body marker may include marking the second type of second probe marker on the body marker when a distance between the position of the first type of first probe marker and the identified position is less than or equal to a threshold distance.

The threshold distance may be set based on manipulation by a user.

The method may further include deleting the first type of first probe marker from the body marker.

The first type of first probe marker may indicate that the number of its related ultrasound images is 1, and the second type of second probe marker may indicate that the number of its related ultrasound images is two or more.

The second type of second probe marker may indicate a result value obtained by adding a number of first ultrasound image to a number of second ultrasound image.

The first type of first probe marker may include one head portion and one body portion, and the second type of second probe marker may include one head portion and the same number of body portions as the result value.

The second type of second probe marker may include a number corresponding to the result value.

The method may further include: storing the body marker with the second type of second probe marker marked thereon and the first and second ultrasound images; displaying the stored body marker according to a user's request to retrieve an image of the object; and when the second type of second probe marker is selected by the user from the body marker, displaying the first and second ultrasound images as ultrasound images related to the second type of second probe marker.

The method may further include: identifying a position of the probe used to obtain a third ultrasound image in the body marker; and changing the second type of second probe marker to a second type of third probe marker according to a result of comparing a position of the second type of second probe marker with the position of the probe used to obtain the third ultrasound image, and the second type of third probe marker indicates a value obtained by adding 1 to the result value.

BRIEF DESCRIPTION OF THE DRAWINGS

These and/or other aspects will become apparent and more readily appreciated from the following description of the embodiments, taken in conjunction with the accompanying drawings in which:

FIG. 1 is a block diagram illustrating an ultrasound diagnosis apparatus according to an exemplary embodiment;

DETAILED DESCRIPTION

Figure 2A:
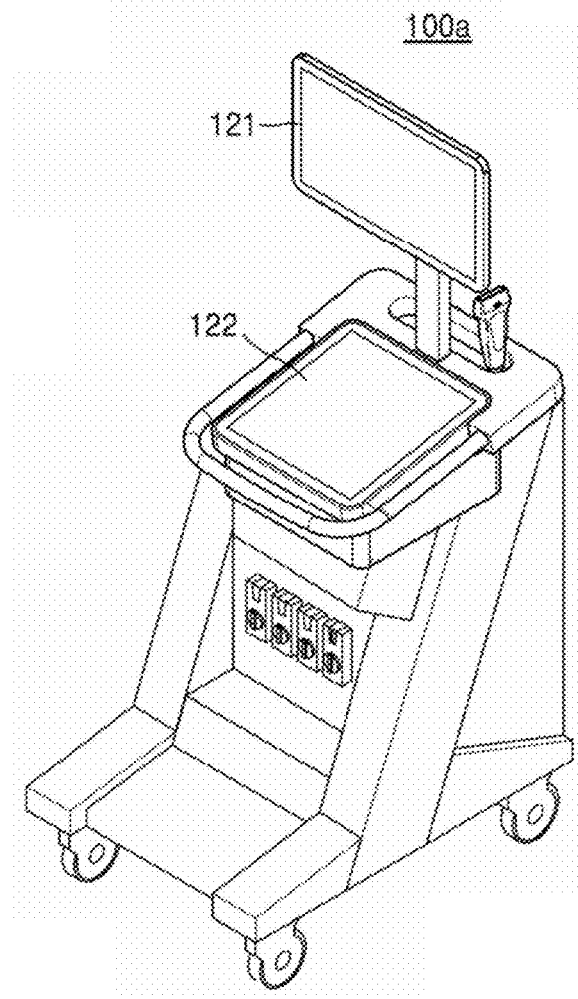
FIGS. 2a, 2b, and 2c are diagrams respectively illustrating an ultrasound diagnosis apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

As used herein, the term "and/or" includes any and all combinations of one or more of the associated listed items. Expressions such as "at least one of," when preceding a list of elements, modify the entire list of elements and do not modify the individual elements of the list.

Terms such as "part" and "portion" used herein denote those that may be embodied by software or hardware. According to exemplary embodiments, a plurality of parts or portions may be embodied by a single unit or element, or a single part or portion may include a plurality of elements.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

In the present specification, ordinal numbers 'first', 'second', and 'third' in a 'first ultrasound image', a 'second ultrasound image', and a 'third ultrasound image' indicate the order in which the ultrasound images are obtained. In other words, the second ultrasound image is obtained after obtaining the first ultrasound image, and the third ultrasound image is obtained after obtaining the second ultrasound image.

Furthermore, in the present specification, ordinal numbers 'first' 'second', and 'third' in a 'first probe marker', a 'second probe marker', and a 'third probe marker' indicate the order in which the probe markers are marked on a body marker. In other words, the second probe marker is marked on the body marker after marking the first probe marker thereon, and the third probe marker is marked on the body marker after marking the second probe marker thereon.

Hereinafter, embodiments will be described in detail with reference to the accompanying drawings.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus that is portable, moveable, mobile, or hand-held. Examples of the ultrasound diagnosis apparatus 100 of a portable type may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control an ultrasound receiver 115 to generate ultrasound data by converting reception signals received from the probe 20 from analog to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data.

For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, a button, a keypad, a mouse, a trackball, a jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

Figure 2B:
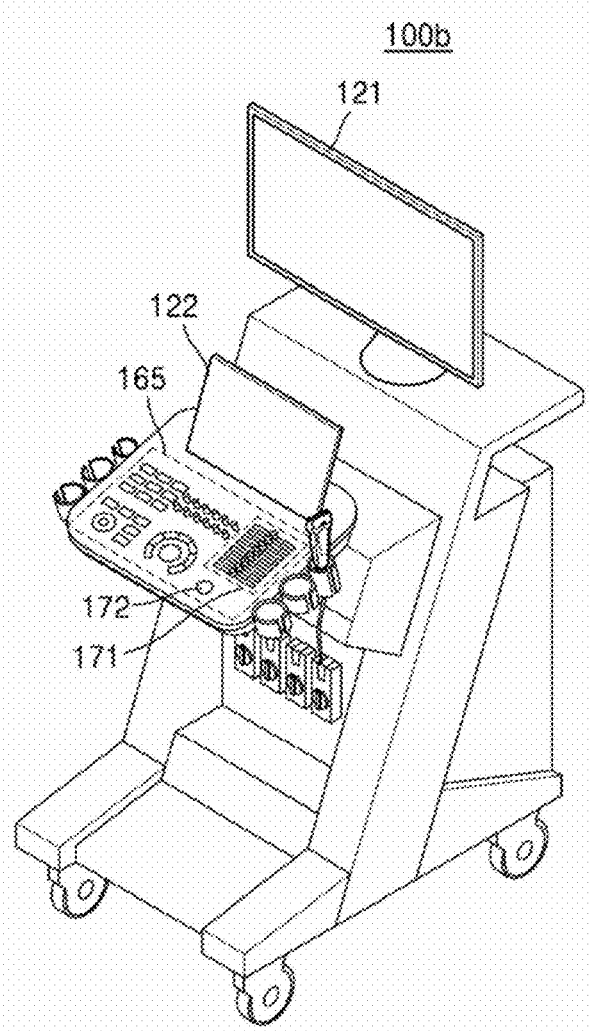
Figure 2C:
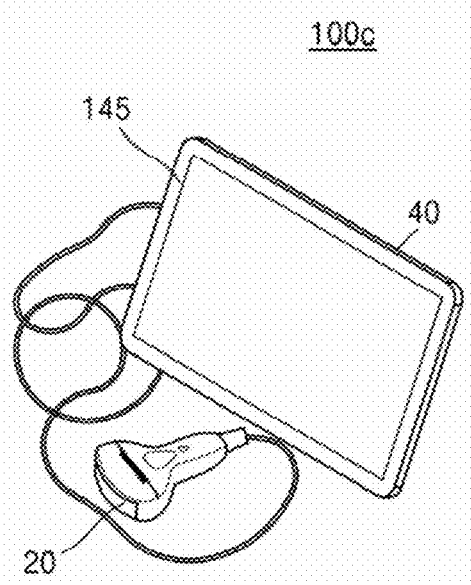

FIGS. 2A, 2B, and 2C are diagrams illustrating ultrasound diagnosis apparatus according to an exemplary embodiment.

Referring to FIGS. 2A and 2B, ultrasound diagnosis apparatuses 100a and 100b may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100a and 100b. The main display 121 and the sub-display 122 may provide graphical user interfaces (GUI), thereby receiving a user's inputs of data to control the ultrasound diagnosis apparatus 100a and 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100a and 100b may control the display of the ultrasound image on the main display 121 by using the input control data.

Referring to FIG. 2B, the ultrasound diagnosis apparatus 100*b* may include a control panel 165. The control panel 165 may include buttons, trackballs, jog switches, or knobs, and may receive data to control the ultrasound diagnosis apparatus 100*b* from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100*b* may keep displaying a frame image at that time point.

The buttons, trackballs, jog switches, and knobs included in the control panel 165 may be provided as a GUI to the main display 121 or the sub-display 122.

Referring to FIG. 2C, an ultrasound diagnosis apparatus 100*c* may include a portable device. Examples of the ultrasound diagnosis apparatus 100*c* that is portable may include smart phones including probes and applications, laptop computers, personal digital assistants (PDAs), or tablet PCs, but an exemplary embodiment is not limited thereto.

The ultrasound diagnosis apparatus 100*c* may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100*c*, and a GUI.

Figure 3:
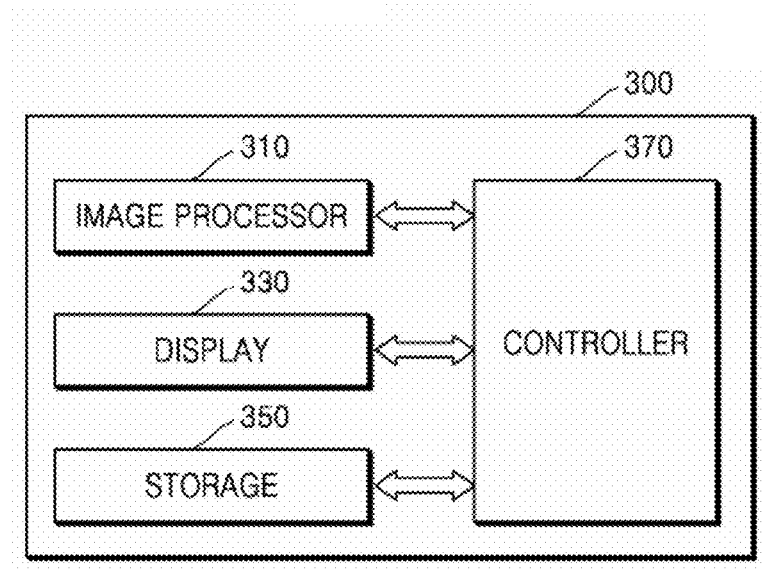
FIG. 3 is a block diagram of a configuration of an ultrasound diagnostic apparatus according to an embodiment.

FIG. 3 is a block diagram of a configuration of an ultrasound diagnosis apparatus 300 according to an embodiment.

Referring to FIG. 3, the ultrasound diagnosis apparatus 300 may include an image processor 310, a display 330, a storage 350, and a controller 370. At least one of the image processor 310, the storage 350, and the controller 370 may be implemented as a processor.

The image processor 310 obtains an ultrasound image of an object. Although not shown in FIG. 3, the image processor 310 may obtain an ultrasound image based on a reflected signal obtained via a probe of the ultrasound diagnosis apparatus 300.

The display 330 displays an ultrasound image of the object. Furthermore, the display 330 may display a body marker corresponding to the object. A body marker may have a shape similar to that of a part of an object being imaged, such as the liver, heart, uterus, brain, breast, and abdomen. A user may select a body marker having a shape similar to that of the part of the object from among various types of pre-stored body markers.

A body marker may include a probe marker, and the probe marker indicates a position and an orientation of a probe used to capture an ultrasound image. For example, when an ultrasound image is captured from a region located at a lower left side of a nipple of a breast, a probe marker may be marked on a lower left side with respect to a center of a body marker.

A probe marker may be marked at a position designated by the user on a body marker before or after obtaining an ultrasound image. According to an embodiment, when it is possible to track a position of the probe, a probe marker may be automatically marked at a point corresponding to the tracked position of the probe on a body marker.

When imaging of the object is completed, the storage 350 stores an ultrasound image of the object and a body marker. A body marker may be used to retrieve an ultrasound image of the object and identify a location where the ultrasound image is captured.

The controller 370 controls operations of the image processor 310, the display 330, and the storage 350. The controller 370 controls the display 330 to display an ultrasound image of the object and a body marker. The controller 370 may manually mark a probe marker related to the ultrasound image on the body marker according to a user input, or automatically mark the probe marker on the body marker by tracking a position of the probe.

According to an embodiment, the controller 370 may determine a shape of a probe marker to be marked on a body marker. The probe marker may be of a first type or a second type. As described below, the controller 370 may select one of a first type of probe marker and a second type of probe marker according to a predefined criterion and mark the selected type of probe marker on the body marker.

According to an embodiment of the disclosure, the first type of probe marker indicates that the number of related ultrasound images is 1, while the second type of probe marker indicates that the number of related ultrasound images is two or more. In other words, the first type of probe marker indicates that a single ultrasound image has been captured at a position of the first type of probe marker on the body marker, while the second type of probe marker indicates that a plurality of ultrasound images have been captured at a position of the second type of probe marker on the body marker. When a plurality of ultrasound images are obtained at neighboring points, it is understood that the corresponding points have a high probability of being a lesion. Thus, the user may easily recognize a point in the object that is highly likely to be a lesion by viewing the second type of probe marker marked on the body marker.

According to an embodiment, the controller 370 may store an ultrasound image of the object and a body marker in the storage 350 and then display the body marker on the display 330 according to a user's request to retrieve an image of the object. Then, when the user selects the probe marker on the body marker, an ultrasound image related to the probe marker selected by the user may be displayed on the display 330.

A method, performed by the ultrasound diagnosis apparatus 300, of marking a probe marker on a body marker will be described in more detail below with reference to FIGS. 4 through 13.

Figure 4:
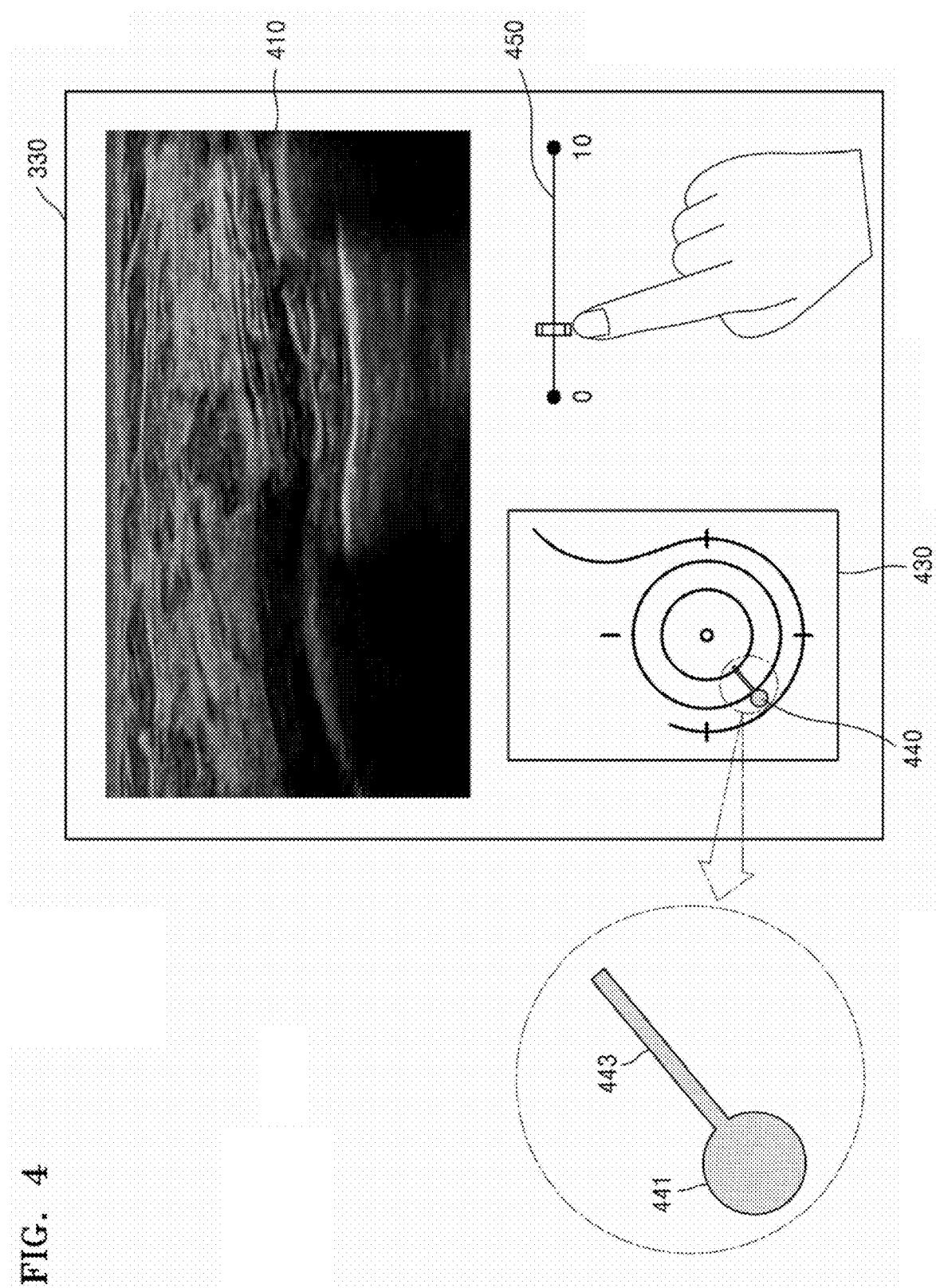
FIG. 4 is an exemplary diagram illustrating a first ultrasound image and a body marker displayed on a display, according to an embodiment.

FIG. 4 is an exemplary diagram illustrating a first ultrasound image 410 and a body marker 430 displayed on the display 330, according to an embodiment.

The ultrasound diagnosis apparatus 300 may display the first ultrasound image 410 of an object on the display 330. Furthermore, as shown in FIG. 4, the display 330 may further display the body marker 430 corresponding to a part of the object being imaged on the display 330.

Before or after obtaining the first ultrasound image 410, the ultrasound diagnosis apparatus 300 identifies a position of a probe used for obtaining the first ultrasound image 410 on the body marker 430 and marks a first type of first probe marker 440 at the identified position. As described above, the first type of first probe marker indicates that the number of ultrasound images related to the first type of first probe marker 440, i.e., the number of first ultrasound images 410, is 1.

The first type of first probe marker 440 may include a head portion 441 and a body portion 443. The head portion 441 may indicate a position of a particular transducer, e.g., a first transducer, from among transducers of the probe, while the body portion 443 indicates positions of the remaining transducers other than the particular transducer from among the transducers of the probe. A direction in which the transducers of the probe are arranged may be identified based on an orientation of the first type of first probe marker 440 including the head portion 441 and the body portion 443.

A shape of the first type of first probe marker 440 shown in FIG. 4 is merely an example, and according to an embodiment, the head portion 441 may have a triangular or quadrilateral shape. Alternatively, the first type of first probe marker 440 may include only one body portion 443.

Referring to FIG. 4, a setting bar 450 may be displayed on the display 330. The setting bar 450 may be used to set a threshold distance which will be described in detail below. The user may increase or decrease the threshold distance through adjustment by the setting bar 450. According to an embodiment, the user may set the threshold distance via an increase/decrease button instead of the setting bar 450 or by entering a corresponding numerical value.

Figure 5:
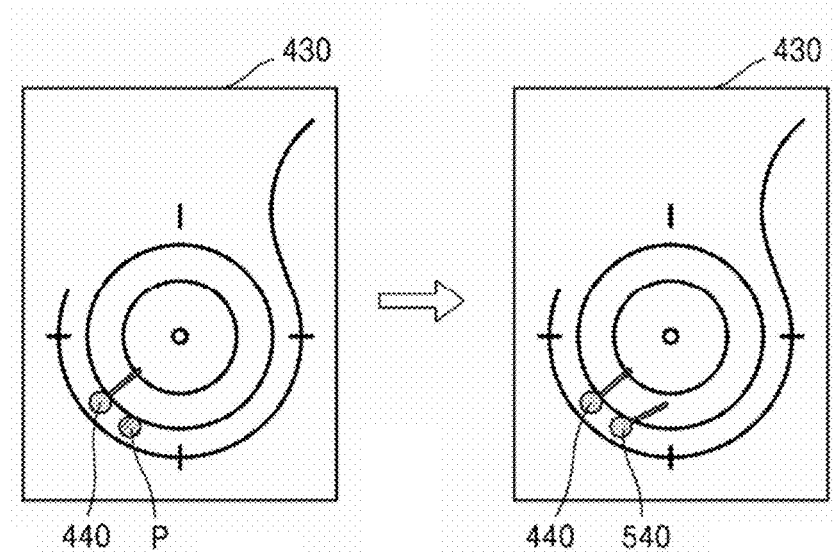
FIG. 5 is a diagram for explaining a method of marking a second probe marker related to a second ultrasound image on a body marker, according to an embodiment.
Figure 6:
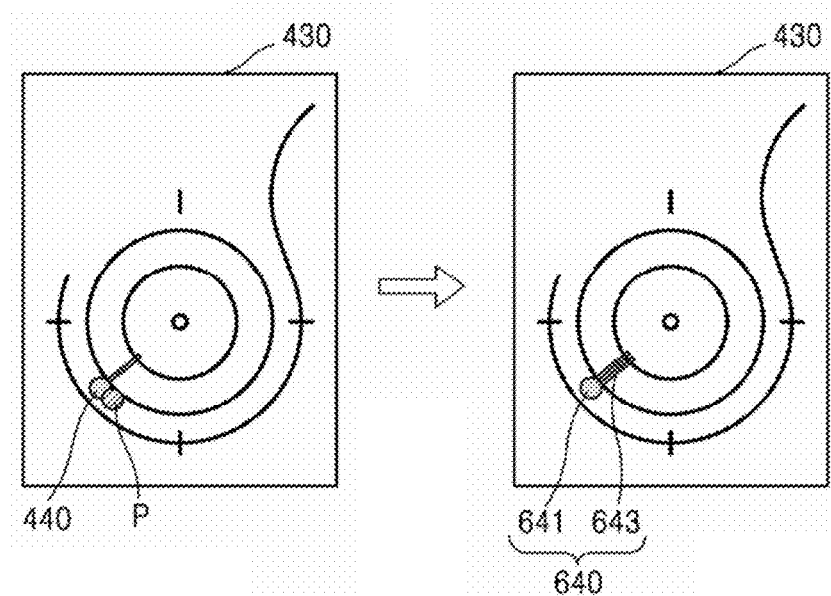
FIG. 6 is a diagram for explaining a method of marking a second probe marker related to a second ultrasound image on a body marker, according to an embodiment.

FIGS. 5 and 6 are diagrams for explaining a method of marking a second probe marker related to a second ultrasound image on a body marker 430, according to an embodiment.

After a first type of first probe marker 440 is marked on the body marker 430, when a second ultrasound image of the object is obtained, the ultrasound diagnosis apparatus 300 may mark a second probe marker related to the second ultrasound image on the body marker 430. In this case, the ultrasound diagnosis apparatus 300 may select one of a first type and a second type according to a predefined criterion and mark the selected type of second probe marker on the body marker 430.

In detail, the ultrasound diagnosis apparatus 300 identifies a position P of the probe used to obtain the second ultrasound image on the body marker 430 and determines a distance between the identified position P and a position of the first type of first probe marker 440. The identified position P may be a position of a particular transducer from among transducers of the probe used to obtain the second ultrasound image, and a position of the first type of first probe marker 440 may be a position of the head portion (441 of FIG. 4). In other words, the ultrasound diagnosis apparatus 300 may determine a distance between the position of a particular transducer from among transducers of the probe used to obtain the second ultrasound image and the position of the head portion 441 of the first type of first probe marker 440. However, this is merely an example of a method of determining a distance between the identified position P and the position of the first type of first probe marker 440, and various methods of measuring the distance may be used.

The ultrasound diagnosis apparatus 300 may compare the distance between the position of the first type of first probe marker 440 and the position P of the probe with a threshold distance and determine the second probe marker as being of a first or second type based on a result of the comparison. For example, when the distance between the position of the first type of first probe marker 440 and the position P of the probe is less than or equal to the threshold distance, the ultrasound diagnosis apparatus 300 may determine a type of the second probe marker as the second type. On the other hand, when the distance between the position of the first type of first probe marker 440 and the position P of the probe is greater than the threshold distance, the ultrasound diagnosis apparatus 300 may determine the type of the second probe marker as the first type.

When the distance between the position P of the probe identified on the body marker 430 and the position of the first type of first probe marker 440 is greater than the threshold distance, as shown in the diagram on the right of FIG. 5, the ultrasound diagnosis apparatus 300 may mark a first type of second probe marker 540 on the body marker 430. The second probe marker 540 being of the first type indicates that the number of ultrasound images related to the first type of second probe marker 540, i.e., the number of second ultrasound images, is 1.

On the other hand, when the distance between the position P of the probe identified on the body marker 430 and the position of the first type of first probe marker 440 is less than or equal to the threshold distance, as shown in the diagram on the right of FIG. 6, the ultrasound diagnosis apparatus 300 marks a second type of second probe marker 640 on the body marker 430. By comparing the diagram of FIG. 6 with that of FIG. 5, it can be seen that the first type of first probe marker 440 is deleted from the body marker 430 as the second type of second probe marker 640 is marked on the body marker 430.

The second probe marker 640 being of the second type indicates that the number of ultrasound images related to the second type of second probe marker 640 is two or more. In other words, as the first type of first probe marker 440 is deleted, the first and second ultrasound images are determined as ultrasound images related to the second type of second probe marker 640.

According to another embodiment, when the position of the first type of first probe marker 440 is identical to the position P of the probe used to obtain the second ultrasound image, the ultrasound diagnosis apparatus 300 may mark the second type of second probe marker 640 on the body marker 430. On the other hand, when the position of the first type of first probe marker 440 is different from the position P of the probe used to obtain the second ultrasound image, the ultrasound diagnosis apparatus 300 may mark the first type of second probe marker 540 on the body marker 430.

The second type of second probe marker 640 may include one head portion 641 and a plurality of body portions 643. In this case, the number of body portions 643 may be equal to the number of ultrasound images related to the second type of second probe marker 640. In other words, when the ultrasound images related to the second type of second probe marker 640 are the first second ultrasound images, two body portions 643 are included in the second type of second probe marker 640. The user may easily recognize how many ultrasound images have been captured at a corresponding position simply by viewing the number of body portions 643 in the second type of second probe marker 640.

Figure 7:
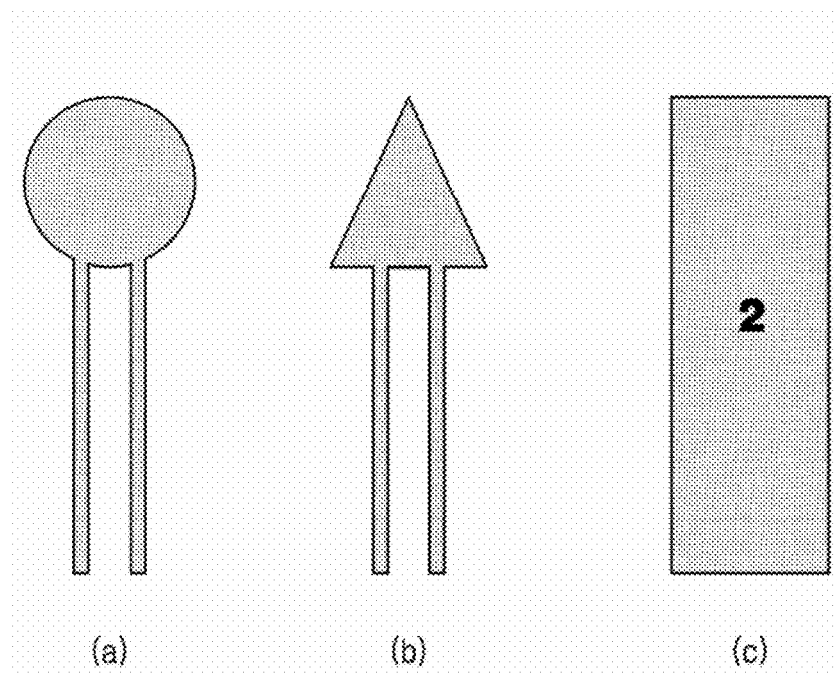
FIG. 7 is exemplary diagram illustrating a second type of probe marker according to an embodiment.

FIG. 7 is exemplary diagram illustrating a second type of probe marker according to an embodiment.

The second type of probe marker may have various shapes. For example, as shown in (a) of FIG. 7, the second type of probe marker may include a circular head portion and linear body portions. As another example, as shown in (b) of FIG. 7, the second type of probe marker may include a triangular head portion and linear body portions. Although (a) and (b) of FIG. 7 each show that the body portions in the second type of probe marker are arranged parallel to each other, each of the body portions may be oriented in the same direction in which the transducers of the probe are arranged when obtaining ultrasound images.

As another example, as shown in (c) of FIG. 7, the second type of probe marker may include a number. Here, the number indicates the number of ultrasound images related to the second type of probe marker. In other words, when ultrasound images related to the second type of probe marker are first and second ultrasound images, the number '2' may be included in the second type of probe marker.

The shapes of the second type of probe markers shown in FIG. 7 are merely an example, and the second type of probe markers may have various shapes distinguishable from those of first type of probe markers indicating that the number of related ultrasound images is 1.

Figure 8:
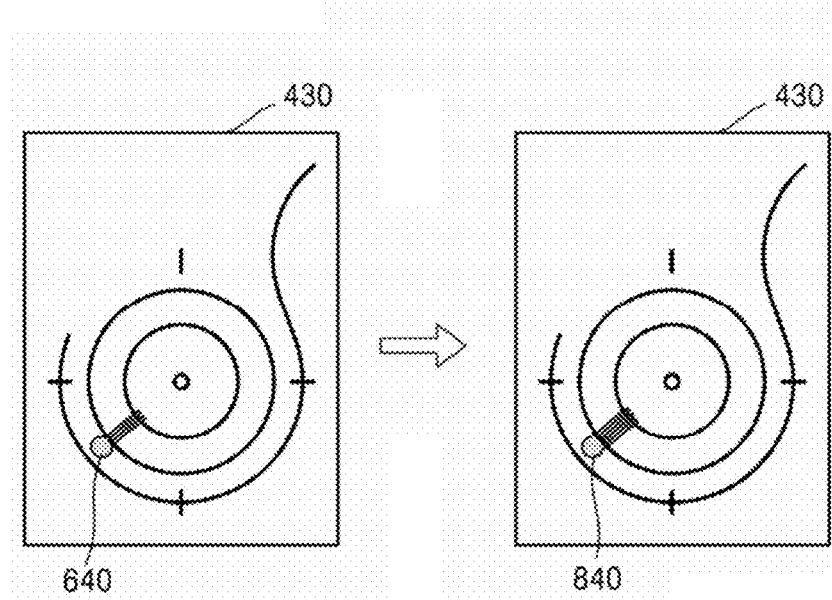
FIG. 8 is a diagram for explaining a method of marking a third probe marker related to a third ultrasound image on a body marker, according to an embodiment.

FIG. 8 is a diagram for explaining a method of marking a third probe marker 840 related to a third ultrasound image on a body marker 430, according to an embodiment.

After a second type of second probe marker 640 is marked on the body marker 430, when a third ultrasound image is obtained, the ultrasound diagnosis apparatus 300 may identify a position of a probe used to obtain the third ultrasound image on the body marker 430 and determine whether a distance between the identified position and a position of the second type of second probe marker 640 is less than or equal to a threshold distance.

When the distance between the identified position and the position of the second type of second probe marker 640 is greater than the threshold distance, the ultrasound diagnosis apparatus 300 marks a first type of third probe marker on the body marker 430. On the other hand, when the distance between the identified position and the position of the second type of second probe marker 640 is less than or equal to the threshold distance, the ultrasound diagnosis apparatus 300 marks a second type of third probe marker 840 on the body marker 430.

The second type of second probe marker 640 is changed to the second type of third probe marker 840 that indicates a value obtained by adding 1 to the number of ultrasound images related to the second type of second probe marker 640. As seen in the diagram on the right of FIG. 8, two body portions included in the second type of second probe marker 640 are changed to three body portions in the second type of third probe marker 840. In other words, first through third ultrasound images are determined as ultrasound images related to the second type of third probe marker 840.

The user may determine that three ultrasound images have been captured at a position of the second type of third probe marker 840 via the second type of third probe marker 840 marked on the body marker 430.

Figure 9:
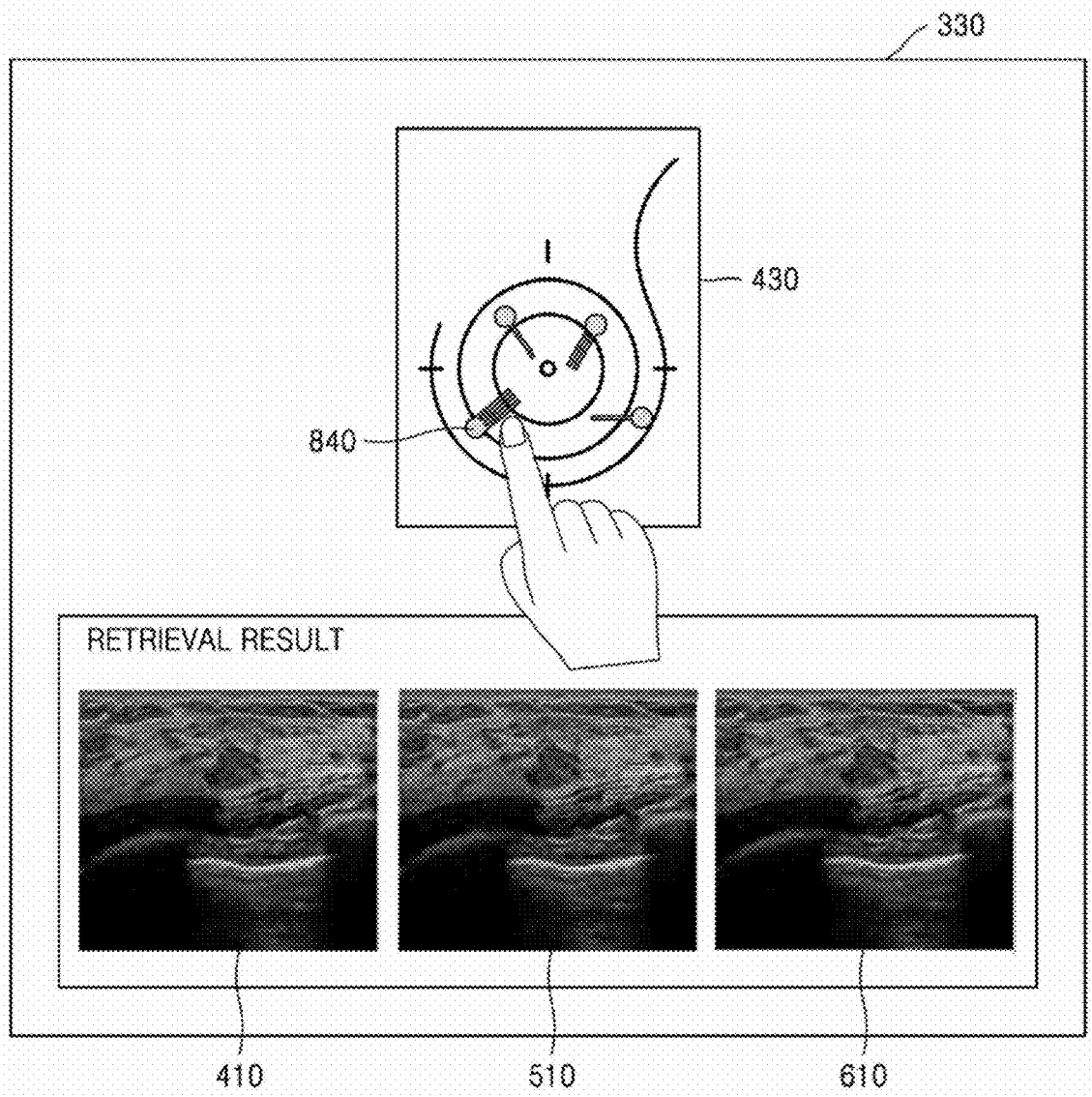
FIG. 9 is a diagram for explaining a method of retrieving an ultrasound image through a body marker, according to an embodiment.

FIG. 9 is a diagram for explaining a method of retrieving an ultrasound image via a body marker 430, according to an embodiment.

When imaging of an object is completed, the ultrasound diagnosis apparatus 300 stores ultrasound images of the object and the body marker 430. Thereafter, when the user requests retrieval of an image of the object, the body marker 430 associated with the object is displayed on the display 330. As shown in FIG. 9, the body marker 430 may include first type of probe markers and second type of probe markers as well as a second type of third probe marker 840.

When the user selects the second type of third probe marker 840 from among the probe markers included in the body marker 430, the ultrasound diagnosis apparatus 300 obtains, from the storage 350, ultrasound images related to the second type of third probe marker 840 from among the ultrasound images of the object and displays the obtained ultrasound images. When the ultrasound images related to the second type of third probe marker 840 are first through third ultrasound images 410, 510, and 610 as described with reference to FIG. 8, the ultrasound diagnosis apparatus 300 may display, on the display 330, the first through third ultrasound images 410, 510, and 610 as the ultrasound images related to the second type of third probe marker 840.

The user may easily recognize a position where multiple images have been captured via the probe markers included in the body marker 430 and easily retrieve several ultrasound images by selecting a probe marker identified as a position where multiple ultrasound images have been captured.

According to an embodiment, when an ultrasound image is obtained via a probe, the ultrasound diagnosis apparatus 300 may acquire orientation information of the probe. The orientation information of the probe may include angles of left-right rotation, forward-backward rotation, and up-down rotation of the probe from among six degrees of freedom. A left-right rotation angle, a forward-backward rotation angle, and an up-down rotation angle may also be referred to as a roll rotation angle, a pitch rotation angle, and a yaw rotation angle, respectively.

A gyro sensor may be embedded in the probe to acquire the orientation information of the probe. When an ultrasound image of the object is obtained, the ultrasound diagnosis apparatus 300 may identify orientation information of the probe when obtaining the ultrasound image and map the identified orientation information to the ultrasound image for storage. As shown in FIG. 9, when the user retrieves an ultrasound image by selecting a probe marker, the ultrasound diagnosis apparatus 300 may also display together the retrieved ultrasound image and orientation information of the probe mapped to the ultrasound image.

Because when an up-down rotation angle of a probe is changed, an orientation of a probe marker is changed accordingly, the up-down rotation angle of the probe may be identified via the probe marker included in a body marker. However, when a left-right or forward-backward rotation angle of the probe is changed, the orientation of the probe marker in the body marker remains unchanged. Thus, the ultrasound diagnosis apparatus 300 may identify orientation information of the probe when obtaining an ultrasound image, and in particular, a left-right rotation angle and a forward-backward rotation angle, and map the identified orientation information to the ultrasound image for storage.

In an embodiment, multiple body portions included in a second type of probe marker may be marked differently from one another according to orientation information of the probe. For example, when a second type of probe marker includes three body portions and orientations of the probe are different from one another when obtaining ultrasound images respectively corresponding to the three body portions, one of the three body portions may be marked as a solid line, another body portion may be marked as a dotted line, and the other body portion may be marked as a dot-dashed line.

Figure 10:
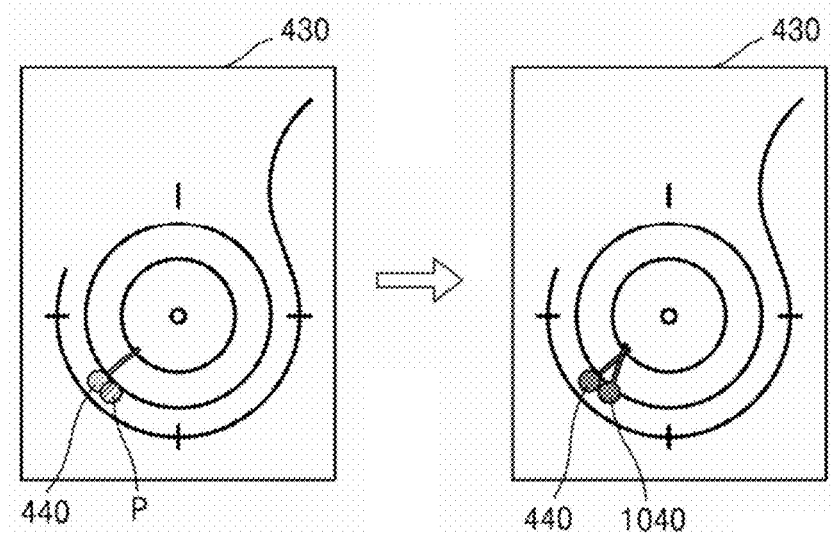
FIG. 10 is a diagram for explaining a method of marking a second probe marker related to a second ultrasound image on a body marker, according to an embodiment.

FIG. 10 is a diagram for explaining a method of marking a second probe marker related to a second ultrasound image on a body marker 430, according to an embodiment.

Although it has been described that when a distance between a position P of the probe when obtaining a second ultrasound image and a position of a first type of first probe marker 440 included in the body marker 430 is less than or equal to a threshold distance, the second type of second probe marker 640 is marked on the body marker 430, according to an embodiment, a first type of second probe marker 1040 may be marked on the body marker 430, wherein the first type of second probe marker 1040 and the first type of first probe marker 440 may be set as one group.

In other words, as seen in the diagram on the right of FIG. 10, even when a distance between the position P of the probe when obtaining the second ultrasound image and the position of the first type of first probe marker 440 included in the body marker 430 is less than or equal to the threshold distance, the first type of second probe marker 1040 is marked near the first type of first probe marker 440.

Furthermore, because the first type of first probe marker 440 and the first type of second probe marker 1040 are set as a group, a color of the first type of first probe marker 440 and the first type of second probe marker 1040 may be determined differently from those of other probe markers not included in the group to indicate that they correspond to the group. For example, when a color of a probe marker that is not in the group is blue, the first type of first probe marker 440 and the first type of second probe marker 1040 included in the group may be marked in red.

Figure 11:
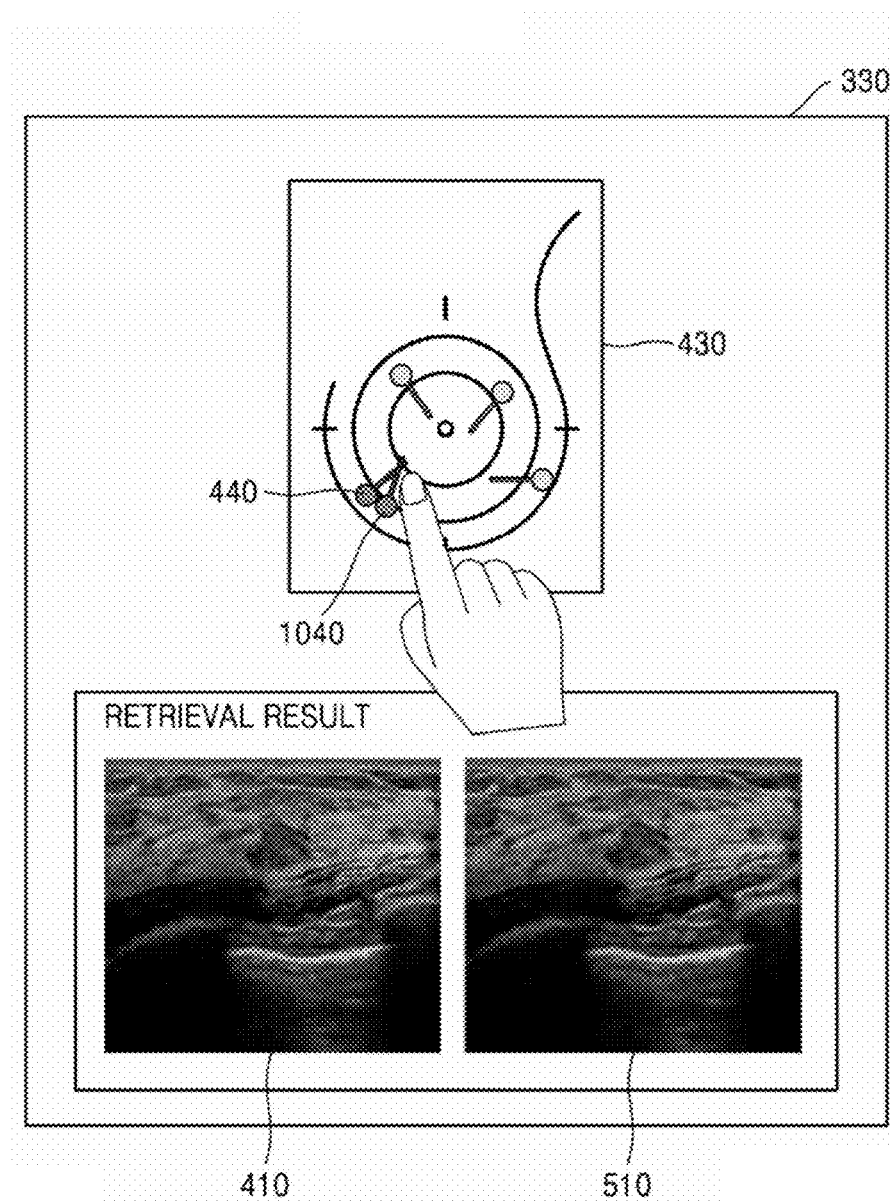
FIG. 11 is a diagram illustrating a method of retrieving an ultrasound image through a body marker shown in FIG. 10, according to an embodiment.

FIG. 11 is a diagram illustrating a method of retrieving an ultrasound image via a body marker 430 shown in FIG. 10, according to an embodiment.

When imaging of an object is completed, the ultrasound diagnosis apparatus 300 stores ultrasound images of the object and the body marker 430. Thereafter, when the user requests retrieval of an image of the object, the body marker 430 associated with the object is displayed on the display 330.

As shown in FIG. 11, the body marker 430 may include a first type of first probe marker 440 and a first type of second probe marker 1040, both being set as a group, and the other probe markers. A color of the first type of first probe marker 440 and the first type of second probe marker 1040 corresponding to the group may be different from a color of a probe marker not included in the group.

When the user selects the first type of first probe marker 440 or the first type of second probe marker 1040 from among the probe markers included in the body marker 430, the ultrasound diagnosis apparatus 300 may display a first ultrasound image 410 related to the first type of first probe marker 440 and a second ultrasound image 510 related to the first type of the second probe marker 1040.

Figure 12:
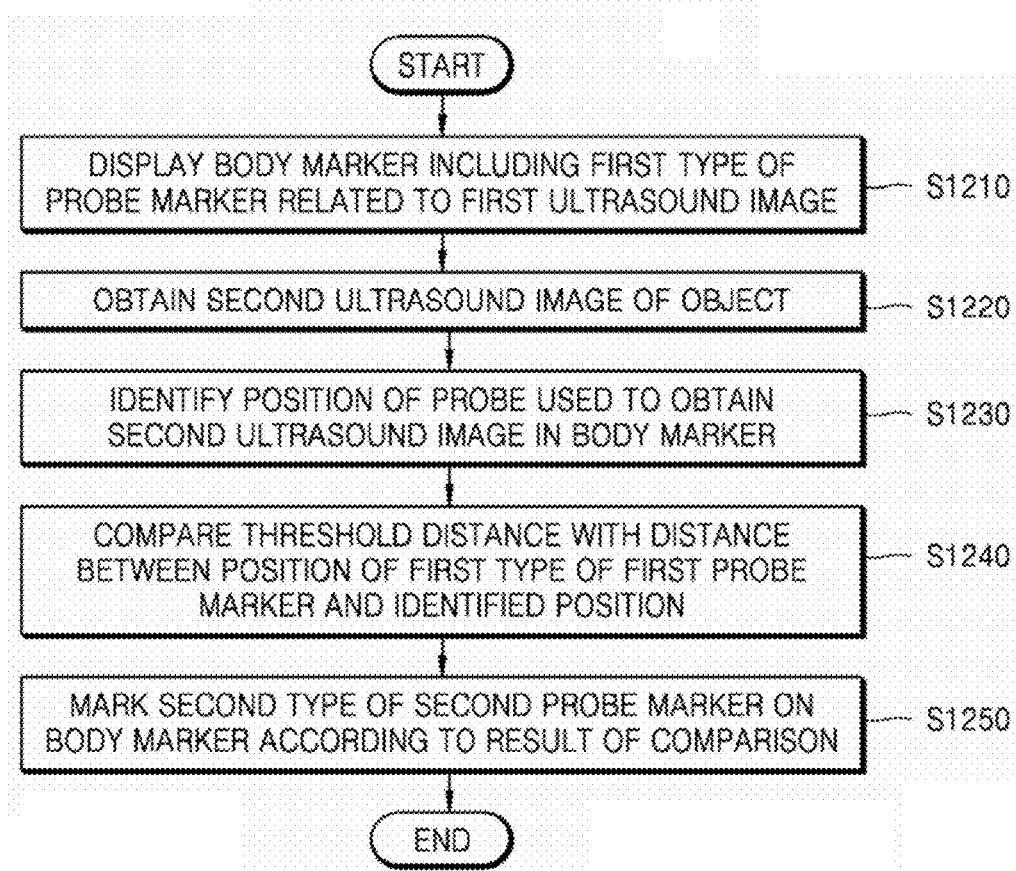
FIG. 12 is a flowchart of a method of managing an ultrasound image, according to an embodiment.

FIG. 12 is a flowchart of a method of managing an ultrasound image, according to an embodiment.

The ultrasound diagnosis apparatus 300 displays a body marker including a first type of first probe marker related to a first ultrasound image of an object (operation S1210).

The ultrasound diagnosis apparatus 300 may mark the first type of first probe marker on the body marker before or after obtaining the first ultrasound image. The first type of first probe marker indicates that the number of ultrasound images related to the first type of first probe marker, i.e., the number of first ultrasound images, is 1.

The ultrasound diagnosis apparatus 300 obtains a second ultrasound image of the object (operation S1220). As a user selects a freeze button while a probe is in contact with a part of the object, the ultrasound diagnosis apparatus 300 may obtain the second ultrasound image of the object.

The ultrasound diagnosis apparatus 300 identifies a position of a probe used to obtain the second ultrasound image on the body marker (operation S1230). The ultrasound diagnosis apparatus 300 may identify a position designated by the user in the body marker as the position of the probe, or track the position of the probe when obtaining the second ultrasound image and identify a point corresponding to the tracked position in the body marker. The position of the probe used to obtain the second ultrasound image may be a position of a particular transducer from among transducers of the probe.

The ultrasound diagnosis apparatus 300 determines a distance between the position of the first type of first probe marker marked on the body marker and the position of the probe identified in operation S1230, and compares the determined distance with a threshold distance (operation S1240).

The ultrasound diagnosis apparatus 300 may determine a distance between a position of a particular transducer from among transducers of the probe used to obtain the second ultrasound image and a position of a head portion of the first type of first probe marker. However, this is merely an example of a method of determining a distance between the identified position of the probe and the position of the first type of first probe marker, and various methods of measuring the distance may be used.

The ultrasound diagnosis apparatus 300 may increase or decrease the threshold distance according to control by the user.

The ultrasound diagnosis apparatus 300 marks a second type of second probe marker on the body marker according to a result of the comparing in operation S1240 (operation S1250).

According to an embodiment, when the distance between the position of the first type of first probe marker and the position of the probe is greater than the threshold distance, the ultrasound diagnosis apparatus 300 marks a first type of second probe marker on the body marker. The second probe marker being of the first type indicates that the number of ultrasound images related to the first type of second probe marker, i.e., the number of second ultrasound images, is 1.

On the other hand, when the distance between the position of the probe identified on the body marker and the position of the first type of first probe marker is less than or equal to the threshold distance, the ultrasound diagnosis apparatus 300 marks a second type of second probe marker on the body marker. As the second type of second probe marker is marked on the body marker, the first type of first probe marker may be deleted from the body marker. The second probe marker being of the second type indicates that the number of ultrasound images related to the second type of second probe marker is two or more.

According to another embodiment, when the position of the first type of first probe marker is identical to the position of the probe used to obtain the second ultrasound image, the ultrasound diagnosis apparatus 300 may mark the second type of second probe marker on the body marker. On the other hand, when the position of the first type of first probe marker is different from the position of the probe used to obtain the second ultrasound image, the ultrasound diagnosis apparatus 300 may mark the first type of second probe marker on the body marker.

According to another embodiment, when the distance between the position of the first type of first probe marker and the position of the probe used to obtain the second ultrasound image is less than or equal to the threshold distance, the ultrasound diagnosis apparatus 300 may mark the first type of second probe marker on the body marker, wherein the first type of first probe marker and the first type of second probe marker may be set as one group.

When imaging of the object is completed, the ultrasound diagnosis apparatus 300 stores ultrasound images of the object and a body marker. Thereafter, when the user requests retrieval of an image of the object, the body marker associated with the object may be displayed. When the user selects a second type of probe marker from among probe markers included in the body marker, the ultrasound diagnosis apparatus 300 obtains ultrasound images related to the second type of probe marker from the storage 350 and displays the obtained ultrasound images.

Moreover, embodiments of the disclosure may be implemented through non-transitory computer-readable recording media having stored therein computer-executable instructions and data. The instructions may be stored in the form of program code, and when executed by a processor, generate a predefined program module to perform a preset operation. Furthermore, when executed by the processor, the instructions may perform preset operations according to embodiments.

According to an embodiment, an ultrasound diagnosis apparatus and a method of managing an ultrasound image obtained by the ultrasound diagnosis apparatus are capable of efficiently managing the ultrasound image through a body marker and a probe marker.

Furthermore, according to an embodiment, an ultrasound diagnosis apparatus and a method of managing an ultrasound image obtained by the ultrasound diagnosis apparatus allow a user to easily recognize a part having a high probability of being a lesion simply by using a body marker.

Furthermore, according to an embodiment, an ultrasound diagnosis apparatus and a method of managing an ultrasound image obtained by the ultrasound diagnosis apparatus allow the user to easily retrieve ultrasound images captured at a part having a high probability of being a lesion.

However, the technical effects achievable by an ultrasound diagnosis apparatus and a method of managing an ultrasound image obtained by the ultrasound diagnosis apparatus according to embodiments are not limited to those described above, and other effects not described above may be clearly understood by those of ordinary skill in the art from the above description.

What is claimed is:

1. An ultrasound diagnosis apparatus comprising:
   an image processor configured to obtain an ultrasound image including a first ultrasound image and a second ultrasound image of an object:
   a display configured to display a body marker having a shape corresponding to an imaged region of the object and a probe marker indicating a position of a probe used to obtain the ultrasound image on the body marker; and
   a controller configured to control the image processor and the display,
   wherein the controller is further configured to:
   control the display to display a first probe marker indicating the position of the probe used to obtain the first ultrasound image in a first type on the body marker,
   determine a distance between the position of the first probe marker and the position of the probe used to obtain the second ultrasound image in the body marker,
   determine the shape of a second probe marker indicating the position of the probe used to obtain the second ultrasound image as the shape of a second type, based on the distance between the position of the first probe marker and the position of the probe used to obtain the second ultrasound image being less than or equal to a threshold distance, and
   control the display to display the second probe marker in the determined shape on the body marker, and
   wherein the shape of the second type is different from the shape of the first type.

2. The ultrasound diagnosis apparatus of claim 1, wherein the controller is further configured to set the threshold distance based on manipulation by an input of a user.

3. The ultrasound diagnosis apparatus of claim 1, wherein the controller is further configured to control the display to delete the first probe marker in the body marker, based on the distance between the position of the first probe marker and the position of the probe used to obtain the second ultrasound image being less than or equal to the threshold distance.

4. The ultrasound diagnosis apparatus of claim 1, wherein the controller is further configured to:
   control the display so that the probe marker of the first type indicates that a number of ultrasound images obtained at the position of the probe marker is 1, and
   control the display so that the probe marker of the second type indicates that the number of ultrasound images obtained at a neighboring point less than or equal to the threshold distance from the position of the probe marker is two or more.

5. The ultrasound diagnosis apparatus of claim 4, wherein the probe marker of the first type includes one head portion and one body portion, and
   the probe marker of the second type includes one head portion and the same number of body portions as the number of ultrasound images obtained at the neighboring point less than or equal to the threshold distance from the position of the probe marker.

6. The ultrasound diagnosis apparatus of claim 4, wherein the probe marker of the second type includes a number shape indicating the number of ultrasound images obtained at the neighboring point less than or equal to the threshold distance from the position of the probe marker.

7. The ultrasound diagnosis apparatus of claim 4, wherein the image processor is further configured to obtain a third ultrasound image of the object,
   wherein the controller is further configured to:
   determine the distance between the position of a third probe marker and the position of the probe used to obtain the second ultrasound image in the body marker,
   control the display to delete the second probe marker and display the third probe marker of the second type in the body marker, based on the distance between the position of the second probe marker and the position of the probe used to obtain the third ultrasound image being less than or equal to the threshold distance.

8. The ultrasound diagnosis apparatus of claim 1,
   further comprising a storage configured to store the obtained ultrasound images from the image processor and the body marker displaying at least one of the first probe marker and the second probe marker,
   wherein the controller is further configured to;
   control the display to display the stored body marker based on a request from the user to retrieve an image of the object r obtain the ultrasound images obtained at a neighboring point less than or equal to the threshold distance from the position of the second probe marker from the storage, and
   control the display to display the ultrasound images obtained from the storage.

9. A method of managing an ultrasound image, using an ultrasound diagnosis apparatus including an image processor configured to obtain an ultrasound image including a first ultrasound image and a second ultrasound image of an object and a display configured to display a body marker having a shape corresponding to an imaged region of the object and a probe marker indicating a position of a probe used to obtain the ultrasound image on the body marker, the method comprising:
   displaying a first probe marker indicating the position of the probe used to obtain the first ultrasound image in a first type on the body marker;
   determining a distance between the position of the first probe marker and the position of the probe used to obtain the second ultrasound image in the body marker;

determining the shape of a second probe marker indicating the position of the probe used to obtain the second ultrasound image as the shape of a second type, based on the distance between the position of the first probe marker and the position of the probe used to obtain the second ultrasound image being less than or equal to a threshold distance; and displaying the second probe marker in the determined shape on the body marker, and wherein the shape of the second type is different from the shape of the first type.

10. The method of claim 9, further comprising setting the threshold distance based on manipulation by an input of a user.

11. The method of claim 9, further comprising deleting the first probe marker in the body marker, based on the distance between the position of the first probe marker and the position of the probe used to obtain the second ultrasound image being less than or equal to the threshold distance.

12. The method of claim 9, wherein the probe marker of the first type indicates that a number of ultrasound images obtained at the position of the probe marker is 1, and the second probe marker of the second type indicates that the number of ultrasound images obtained at a neighboring point less than or equal to the threshold distance from the position of the probe marker is two or more.

13. The method of claim 12, wherein the probe marker of the first type includes one head portion and one body portion, and the probe marker of the second type includes one head portion and the same number of body portions as the number of ultrasound images obtained at the neighboring point less than or equal to the threshold distance from the position of the probe marker.

14. The method of claim 12, wherein the probe marker of the second type includes a number shape indicating the number of ultrasound images obtained at the neighboring point less than or equal to the threshold distance from the position of the probe marker.

15. The method of claim 12, further comprising:

obtaining a third ultrasound image of the object from the image processor;

determining the distance between the position of a third probe marker and the position of the probe used to obtain the second ultrasound image in the body marker;

deleting the second probe marker and displaying the third probe marker of the second type in the body marker, based on the distance between the position of the second probe marker and the position of the probe used to obtain the third ultrasound image being less than or equal to the threshold distance.

16. The method of claim 9, wherein the ultrasound diagnosis apparatus further includes a storage configured to store the obtained ultrasound images from the image processor and the body marker displaying at least one of the first probe marker and the second probe marker, the method further comprising:

displaying the stored body marker based on a request from the user to retrieve an image of the object;

obtaining the ultrasound images obtained at a neighboring point less than or equal to the threshold distance from the position of the second probe marker from the storage and displaying the ultrasound images obtained from the storage.

* * * * *